United States Patent [19]

Ohmi et al.

[11] Patent Number: 5,444,379
[45] Date of Patent: Aug. 22, 1995

[54] ELECTRIC CONDUCTIVITY MEASURING CELL

[75] Inventors: Tadahiro Ohmi, 2-1-17-301, Komegafukuro, Aoba-ku, Sendai-city, Miyagi-prefecture; Yoshio Ishihara, Tsuchiura; Ryosuke Fukushima, Kyoto, all of Japan

[73] Assignees: Horiba, Ltd., Kyoto; Nippon Sanso Corporation, Tokyo; Tadahiro Ohmi, Miyagi, all of Japan

[21] Appl. No.: 893,244

[22] Filed: Jun. 3, 1992

[30] Foreign Application Priority Data

Jun. 6, 1991 [JP] Japan ............... 3-051481 U

[51] Int. Cl.6 .................................... G01N 27/02
[52] U.S. Cl. .................... 324/450; 204/408; 324/448
[58] Field of Search ............ 324/439, 450, 448, 449, 324/441; 73/61.44, 61.47, 61.55, 866.5; 204/400, 272, 408

[56] References Cited

U.S. PATENT DOCUMENTS

| | | | |
|---|---|---|---|
| 2,258,045 | 10/1941 | Christie | 324/448 |
| 2,350,378 | 6/1944 | Wallace | 324/448 |
| 4,227,151 | 10/1980 | Ellis et al. | 324/441 |
| 4,455,213 | 6/1984 | Neti et al. | 204/408 |

FOREIGN PATENT DOCUMENTS

| | | | |
|---|---|---|---|
| 968548 | 2/1958 | Germany | |
| 2932137 | 2/1981 | Germany | 324/450 |

OTHER PUBLICATIONS

Les Point sur les capteurs 17: Mesure de conductivit, by D. Mansion, Nouvel Automatisme, vol. 29, No. 48, Sep. 1984, Paris/France, pp. 56–62.
Patent Abstracts of Japan, vol. 10, No. 344, (p. 518) (2400) Nov. 20, 1986, and Japan A-61 145 441 (Nippon Ester), Jul. 3, 1986.
French patent application No. 2 531 536.

Primary Examiner—Maura K. Regan
Attorney, Agent, or Firm—Price, Gess & Ubell

[57] ABSTRACT

An electric conductivity-measuring cell comprises a pressure container serving also as an outer electrode and provided with an inlet port of a liquid to be measured and an outlet port and an inner electrode provided within said pressure container so as to simplify it in construction and improve a measurement in accuracy.

26 Claims, 11 Drawing Sheets

ELECTRIC CONDUCTIVITY MEASURING CELL

BACKGROUND OF THE INVENTION

1. Field of the Invention

The present invention relates to an electric conductivity-measuring cell used for measuring an electric conductivity of chemical substances, which are used in a production of semiconductors and are gaseous at normal temperature and pressure. The measuring cell can operate under condition of liquefied gases and for a control of water quality of industrial water, water supplied for a boiler, various kinds of washing water and the like, and in particular to an electric conductivity-measuring cell suitable for a measurement of an electric conductivity of liquids, which exist under high-temperature and high-pressure conditions, such as a primary cooling water in a nuclear power plant.

2. Description of the Prior Art

High-purity halogen gases, inorganic hydrides, such as hydrogen halide gases, and the like have been used as dry etching gases in the production of semiconductors and various kinds of gas, such as $SiH_4$, $Si_2H_6$ and $SiH_2Cl_2$, have been used in the formation of thin films of Si, $SiO_2$, $Si_3N_4$ and the like. If such gases have a remarkably very small quantity (for example a ppb-level) of impurities contained in these gases, a bad influence upon a manufacturing process of LSI and the like by these impurities is increased as a circuit pattern is reduced to very find details and also a gas piping system itself can be seriously influenced. So, it has been desired in the industry to accurately measure any concentration of the impurities at a ppb-level and to monitor them.

In addition, various kinds of impurities, such as corrosion products by an electrolysis, are formed by an operation of a reactor in reactor-cooling water circulating through a primary cooling system of a boiling water reactor. In particular, when electric conductivity is increased with an increase of electrolyzed components, a rate of corrosion of structures in such a system is rapidly increased and corrosion products are further radioactivated by neutrons to increase a radioactive level within the system while electrolytic impurities are settled on a surface of fuel rods to hinder a smooth thermal conductance. As a result, the operating efficiency of the reactor is reduced, so that the primary cooling water must be suitably refined to a high purity level or newly replenished to be controlled so that a constant water quality may be always kept. In particular, the control of the electric conductivity as an index of the quantity of said electrolyzed components is an important item for the control of water quality of the primary cooling water.

SUMMARY OF THE INVENTION

The present invention has been achieved paying attention to the above described matters and it is an object of the present invention to provide an electric conductivity-measuring cell capable of measuring an electric conductivity of a liquid with high accuracy and further inexpensively.

In order to achieve the above described object, an electric conductivity-measuring cell according to the present invention comprises a pressure container serving also as an outer electrode and provided with an inlet port for a liquid to be measured and an outlet port and an inner electrode provided within the pressure container.

In this case, an inner surface of the pressure container and an outer surface of the inner electrode may be subjected to an electro-polishing, an oxidative passivating treatment or a fluorinative passivating treatment.

A cylindrical portion connected with the pressure container is provided with a stepped portion formed therewithin and, a diffused-diameter portion is formed midway in the longitudinal direction of the inner electrode. A first insulating spacer comprises a cylindrical reduced-diameter member placed in an airtight manner in a separate cylindrical diffused-diameter member having a larger diameter and a smaller length as compared with those of the cylindrical reduced-diameter member is a tapered manner. A first sealing ring is positioned on one side of the inner electrode so that the first sealing ring may be closer to the diffused diameter portion of the inner electrode. A second sealing ring is positioned on a reduced-diameter portion of the first insulating spacer, a stepped second spacer and a thrust bearing is placed on the other side of the inner electrode so that the second insulating spacer may be closer to the diffused-diameter portion of the inner electrode, whereby the first sealing ring may be pressedly put between the first insulating spacer and the diffused-diameter portion of the inner electrode and the second sealing ring may be pressedly put between the stepped portion of the cylindrical portion and the first insulating spacer by fastening a cap nut engaged with the cylindrical portion.

In this case, the diffused-diameter portion of the inner electrode may be provided with a concave portion to fixedly hold the first sealing ring by means of the concave portion.

In the above described electric conductivity-measuring cell, the liquid to be measured is introduced into the pressure container through the inlet port to enable a measurement of the electric conductivity thereof within the time period when it passes through a gap between the pressure container serving also as the outer electrode and the inner electrode. The liquid to be measured is discharged through the outlet port.

In the above described electric conductivity-measuring cell, the stepped first insulating spacer is airtightly put in a separate cylindrical diffused-diameter member having a larger diameter and a smaller length as compared with those of the cylindrical reduced-diameter member in a tapered manner and comprises the reduced-diameter portion and the diffused-diameter portion, so that the diffused-diameter portion and the reduced-diameter portion can be individually finished, in particular both end faces of the diffused-diameter portion, acting as sealing surfaces of the first insulating spacer can be mirror-finished.

Accordingly, it is unnecessary to press the sealing rings by an excessive power and thus the first insulating spacer is not damaged.

In addition, in the case where the diffused-diameter portion of the inner electrode is provided with a curved concave portion on a sealing surface thereof to fixedly hold the first sealing ring, not only its airtightness can be improved but also a positional relation between the inner electrode and the pressure container as the outer electrode can be fixedly set at a desired positional relationship, so that the measurement can be achieved with higher accuracy.

BRIEF DESCRIPTION OF THE DRAWINGS

A first preferred embodiment of the present invention is shown in FIGS. 1 to 10, in which.

A second preferred embodiment of the present invention is shown in FIGS. 11 to 13, in which.

DETAILED DESCRIPTION OF THE PREFERRED EMBODIMENTS

Figure 1:
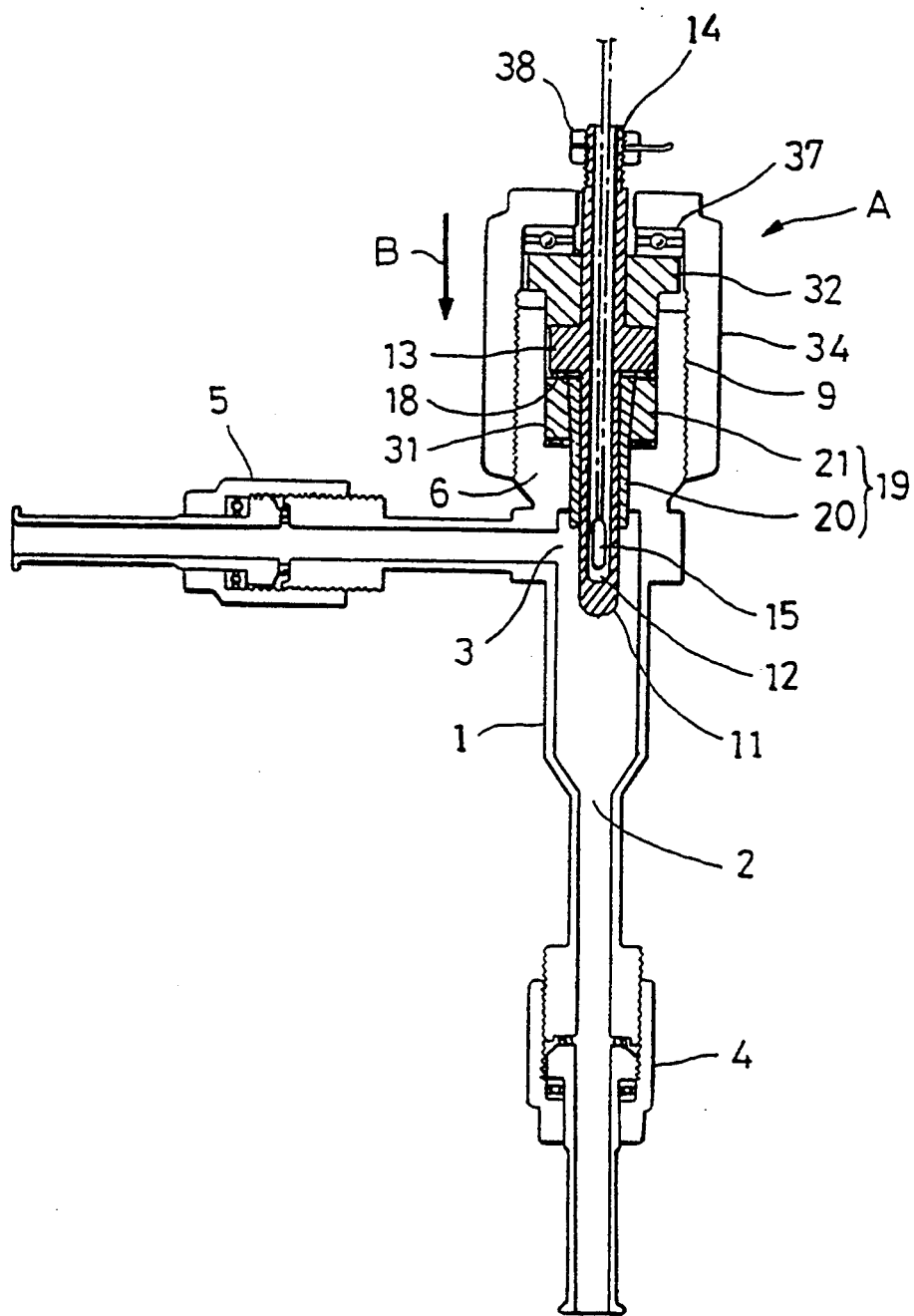
FIG. 1 is a longitudinal sectional view showing an electric conductivity-measuring cell.

FIG. 1 is a longitudinal cross sectional view showing an electric conductivity-measuring cell A (hereinafter referred to as a cell) according to a first preferred embodiment of the present invention. Referring to FIG. 1, reference number 1 designates a pressure container serving also as an outer electrode electrode. The outer functions on the side of a lower impedance in an alternating bielectrode method and is provided with a inlet port 2 of a liquefied gas to be measured on a lower side thereof and an outlet port 3 of the liquefied gas on an upper thereof. The pressure container 1 is made of corrosion resistant metals, such as stainless steels, and an inner surface of the pressure container 1 is subjected to an electro-polishing, an oxidative passivating treatment or a fluorinative passivating treatment to improve its chemical resistance and corrosion resistance. The pressure container 1 has a highly airtight construction, as described later.

The inlet port 2 is connected with a gas-liquefying apparatus or a liquefied gas cylinder (not shown) through a coupling 4. In addition, the outlet port 3 is connected with pipings to an apparatus for producing semiconductors and the like (not shown) through a coupling 5. A cylindrical member 6 is electrically and mechanically connected with the pressure container 1 and is provided with a cylindrical hole 7 opened at one end and a hole 8 having a diameter smaller than that of the cylindrical hole 7 connected at the other end and a threaded portion 9 formed on an outer circumference thereof, as shown also in FIG. 2. Also an inner surface of the cylindrical member 6 is subjected to an electro-polishing, an oxidative passivating treatment or a fluorinative passivating treatment.

Reference numeral 11 designates an inner electrode arrange concentrically with the pressure container 1 in an upper space within the pressure container 1. That is to say, in cell A as used in this preferred embodiment, a measuring electrode is composed of the pressure container 1 serving also as the outer electrode and the inner electrode 11 arranged in a highly insulating connection with the pressure container 1. It is necessary to determine a cell constant of the measuring electrode depending upon a sample but this cell constant is determined by an inner surface area of the pressure container 1 in a portion where the pressure container 1 and the inner electrode 11 are opposite to each other, an area of an outer surface, with which the inner electrode 11 is connected, and a distance from the pressure container 1 to the inner electrode 11.

Figure 2:
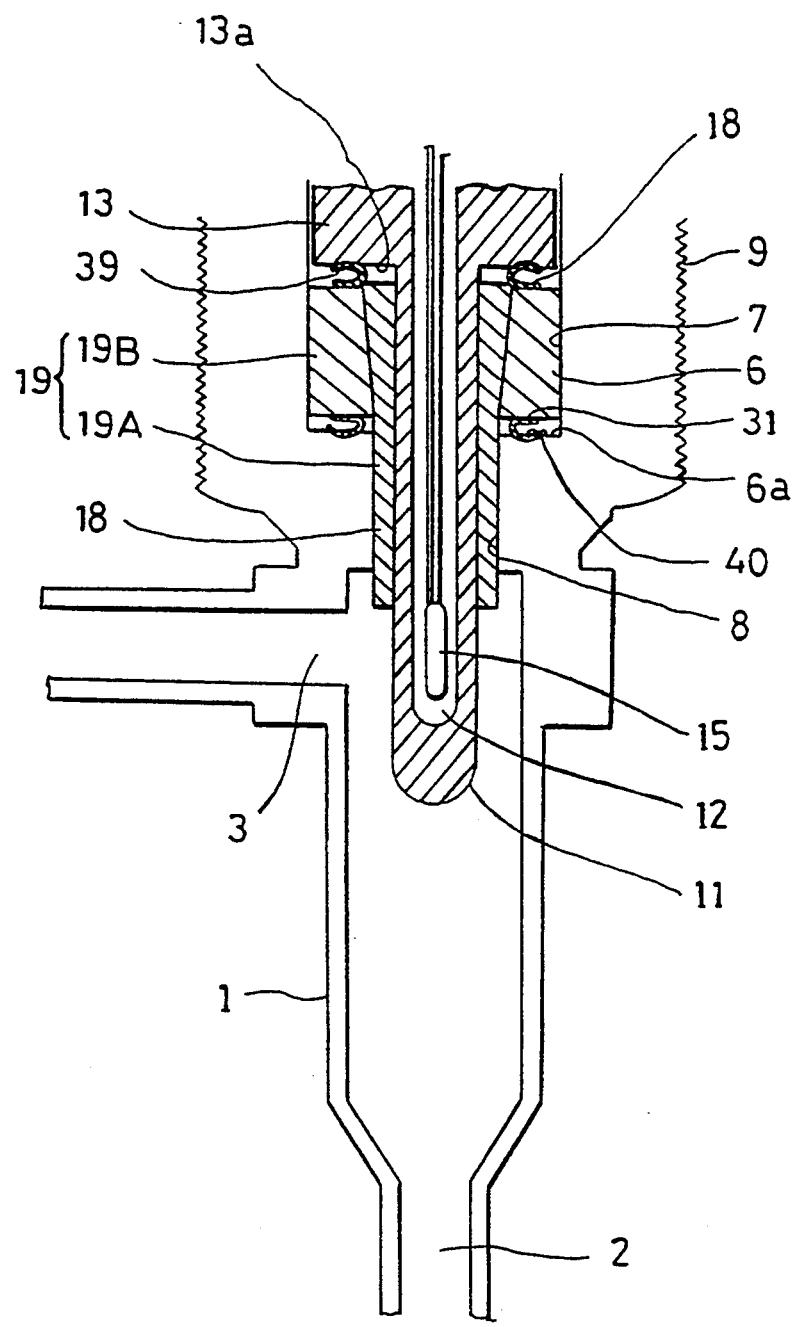
FIG. 2 is a longitudinal sectional view showing a construction of essential parts of the cell.
Figure 3:
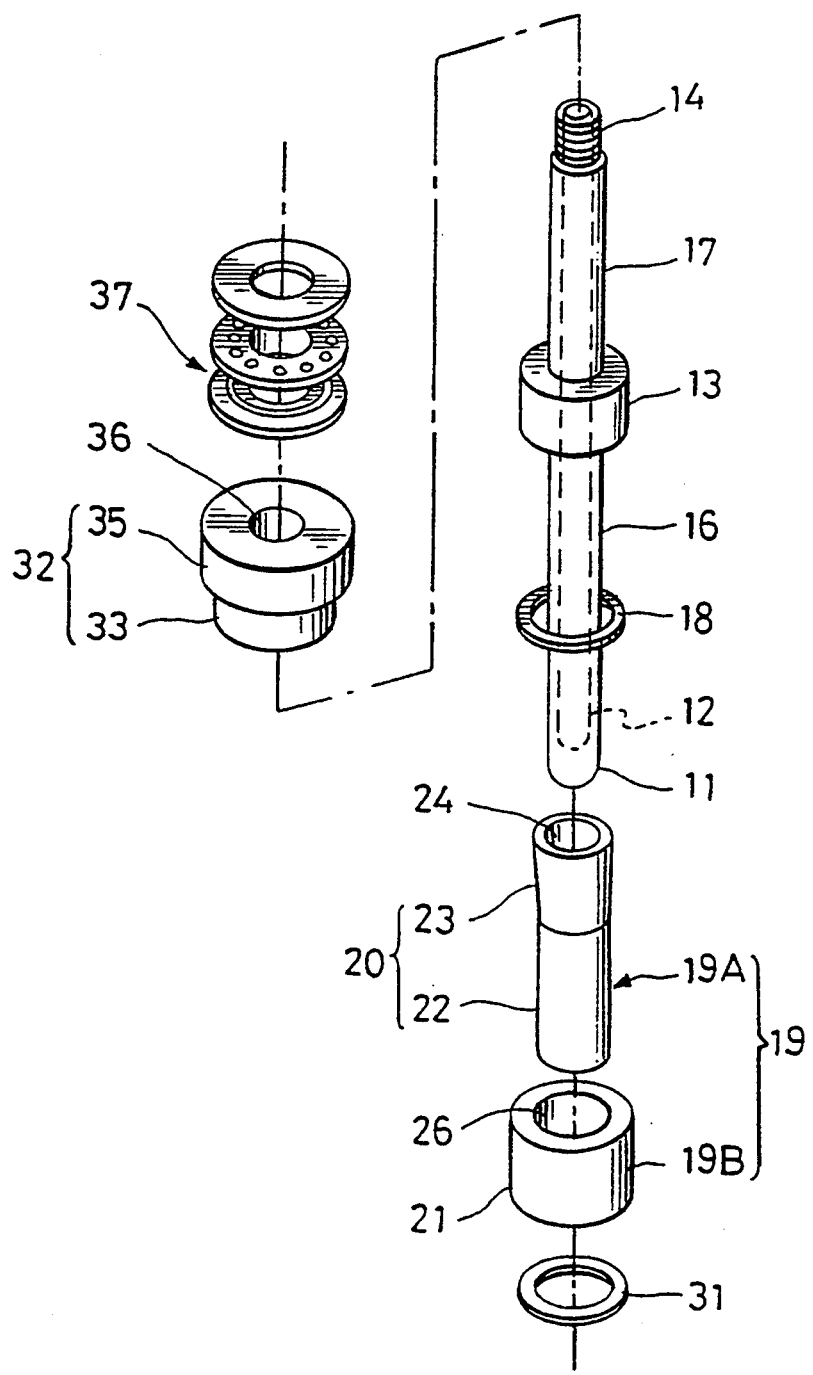
FIG. 3 is a disintegrated perspective view showing a construction of an inner electrode and a sealing construction.

The inner electrode 11 is, as shown also in FIGS. 2, 3, provided with a hollow member 12 opened on the side of one end and closed on the side of the other end and a diffused-diameter portion 13 having a diameter smaller than an inside diameter of the cylindrical member 6 formed in a midway portion in the longitudinal direction. An outside diameter of the diffused-diameter portion 13 of the inner electrode is set so that a clearance having an appointed high insulating power may be formed between the inner electrode 11 and the inner surface of the cylindrical member 6 under a condition that the inner electrode 11 is arranged within the pressure container 1, as shown in FIG. 1.

The inner electrode 11 is made of corrosion resistant metal, such as stainless steel, and the outer surface of the inner electrode 11 is subjected to an electro-polishing, an oxidative passivating treatment or a fluorinative passivating treatment. In addition, the inner electrode 11 is provided with a tapped portion 14 formed at an end portion on the opened side thereof and a temperature sensor 15 is inserted into the hollow member 12 from the opened side adjacent the vicinity of a closed portion. The temperature sensor 15 is inserted into an inside of the hollow ember 12 of the inner electrode 11 and is not brought into direct contact with a liquefied gas, so that it is not necessary to subject the temperature sensor 15 to a chemical resisting treatment, a corrosion-resisting treatment and the like. Furthermore, hereinafter a reduced-diameter portion from the diffused-diameter portion 13 of the inner electrode to an end portion on the closed sided is referred to as an inward portion 16 of the inner electrode and a reduced-diameter portion from the diffused-diameter portion 13 of the inner electrode to an end portion of the opened side is referred to as an outward portion 17 of the inner electrode.

Reference numeral 18 designates a C-ring as a first sealing ring made of metals, such as nickel, and put on the inward portion 16 of the inner electrode so as to be adjacent to one side of the diffused-diameter portion 13 of the inner electrode. Reference numeral 19 designates a first stepped insulating spacer put on the inward portion 16 of the inner electrode and composed of a cylindrical reduced-diameter member 20 airtightly put in a separate cylindrical diffused-diameter member 21 having a larger diameter and a smaller length as compared with those of the cylindrical reduced-diameter member 20 in a tapered manner and comprises a reduced-diameter portion 19A and a diffused-diameter portion 19B.

A construction of the first insulating spacer 19 will be below described in detail with reference to FIGS. 3 and 4. The major portion of a trunk portion of the reduced-diameter member 20 is formed so as to have an outside diameter sightly smaller than a diameter of the hole 8 provided between the pressure container 1 and the cylindrical member 6 but a tapered surface 23 is also formed so as to be thicker toward the upper end portion over a certain length from the upper end. The reduced-diameter member 20 is provided with a through hole 24 having a diameter slightly larger than that of the inward portion 16 of the inner electrode at a center of an axis thereof. In addition, the diffused-diameter member 21 has an outside diameter sightly smaller than that of the hole 7 of the cylindrical member 6 and is provided with a through hole 26 surrounded by a tapered surface 25 corresponding to the tapered surface 23 of the reduced-diameter member 20.

The reduced-diameter member 20 and the diffused-diameter member 21 are made of highly insulating materials such as ceramics. Outer surfaces including both end faces of the reduced-diameter member 20 and the diffused-diameter member 21 are subjected to a mirror-polishing, in particular said both end faces 27 and 28 of the diffused-diameter member 21 are subjected to a high mirror-polishing so that Ra (mean roughness on a central line) may be reduced to for example 0.08 $\mu$m or less and a surface accuracy may be improved to an extent of for example 0.5 $\mu$m or less. In addition, the tapered surfaces 23 and 25 of the reduced-diameter member 20 and the diffused-diameter member 21 are improved in airtightness by a mutual rubbing.

Figure 4:
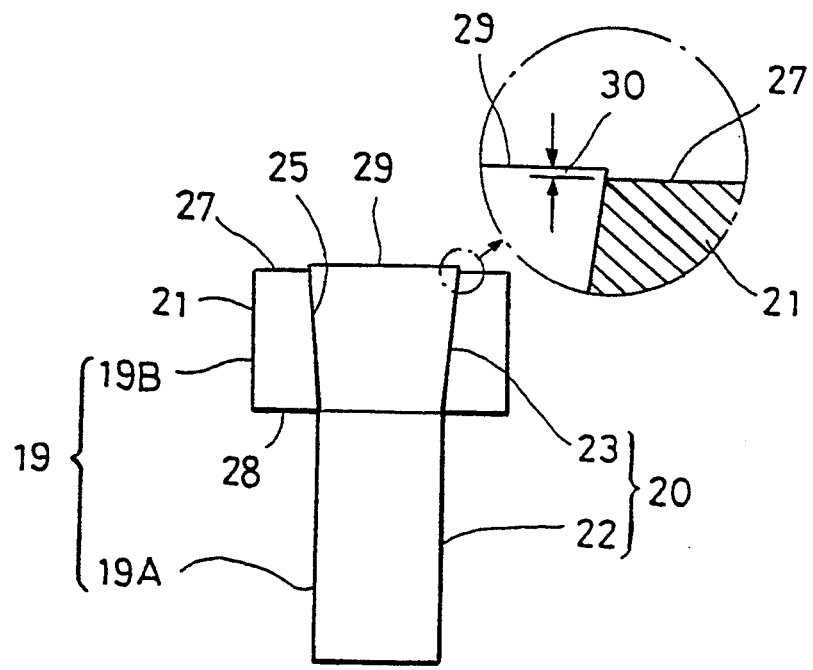
FIG. 4 is a drawing showing one example of a first insulating spacer.

The reduced-diameter member 20 is inserted into through hole 26 of the diffused-diameter member 21 from the side of reduced-diameter thereof and airtightly engaged in a tapered manner, as shown in FIG. 4, to form the stepped first insulating spacer 19 composed of the reduced-diameter portion 19A (consisting of the straight trunk portion 22 of the reduced-diameter member 20) and the diffused-diameter member 19B (substantially consisting of the diffused-diameter member 21), but, as enlargedly shown in FIG. 4, an end face 29 of the reduced-diameter member 20 is adapted to slightly (for example about 0.2 mm at maximum) project from the end face 27 of the diffused-diameter member 21. In short, both end faces 27 and 28 are adapted to form a slight step 30 therebetween.

The reduced-diameter portion 19A of the first insulating spacer 19 having the above described construction is, as shown in FIGS. 1, 2, inserted into the hole 8 of the cylindrical member 6 so that a pointed end thereof may arrive at the vicinity of the outlet port 3 of the pressure container 1. Although the cell constant is determined by the areas of the inner and outer electrodes and the distance from the inner electrode to the outer electrode, as above described, it can be regulated also by regulating a length of the reduced-diameter portion 19A of the first insulating spacer 19 in addition to regulating a length of the inner electrode 11. In addition, the reduced-diameter portion 19A reduces a contribution to the cell constant in the portion serving as a stagnant portion of the liquefied gas in the cell by increasing a substantial length between the inner electrode and the outer electrode in the portion positioned above the outlet port 3 within the pressure container 1 to improve an accuracy of measurement of an electric conductivity meter.

Referring to FIGS. 1 to 3, reference numeral 31 designates a C-ring as a second sealing ring made of metals such as nickel put on the reduced-diameter portion 19A. Reference numeral 32 designates a second insulating spacer put on the outward portion 17 of the inner electrode so as to be adjacent to the other side of the diffused-diameter portion 13 of the inner electrode, composed of a reduced diameter portion 33 having a diameter slightly smaller than that of the hole 7 of the cylindrical member 6 and a diffused-diameter portion 35 having a diameter larger than that of the reduced-diameter portion 33 but slightly smaller than an inside diameter of a cap nut 34 screwed on the cylindrical member 6, and provided with a hole 36 having a diameter slightly larger than that of the outward portion 17 of the inner electrode passing therethrough. Additionally, the second insulating spacer 32 is made of highly insulating materials, such as ceramics, and an outer surface including both end faces of the second insulating spacer 32 is subjected to a mirror-polishing. Reference numeral 37 designates a thrust bearing and reference numeral 38 designates a voltage terminal for applying a voltage to the inner electrode 11.

One example of procedures fore arranging the inner electrode 11 within the pressure container 1 will be below described. The first sealing ring 18 is put on the inward portion 16 of the inner electrode 11 with the temperature sensor 15 inserted into the hollow member 12 so as to be adjacent to one side of the diffused-diameter portion 13 of the inner electrode and then the first insulating spacer 19 is put on the first sealing ring 18. Subsequently, the second sealing ring 31 is put on the reduced-diameter portion 19A of the first insulating spacer 19 while the second insulating spacer 32 is put on the outward portion 17 of the inner electrode 11 so as to be adjacent to the other side of the diffused-diameter portion 13 of the inner electrode and then the thrust bearing 37 is put on the second insulating spacer 32.

The inner electrode 11, on which the respective members have been put in the above described manner, is inserted into the pressure container 1 with the side of the closed portion as the head through the cylindrical member 6. The cap nut 34 is put on the cylindrical member 6 to be screwed up. When the cap nut 34 is screwed up, a torque in the direction of rotation is eased by an action of the thrust bearing 37 and thus a force acts merely in the direction shown by an arrow B in FIG. 1, whereby the first sealing ring 18 is strongly held between one side of the diffused-diameter portion 19B of the first insulating spacer 19 and the diffused-diameter portion 13 of the inner electrode and the second sealing ring 31 between a stepped portion 6a (refer to FIG. 2) of the cylindrical member 6 and the other side of the first insulating spacer 19 without damaging the sealing portion. As a result, the inner electrode 11 is held within the pressure container 1 concentrically with the pressure container 1 and the rings 18, 31 are evenly smashed to seal up the inner electrode 11 and the first insulating spacer 19 by means of the ring 18 and seal up the cylindrical member 6 of the pressure container 1 and the first insulating spacer 19 by means of the ring 31, whereby maintaining an airtightness within the pressure container 1.

Figure 5:
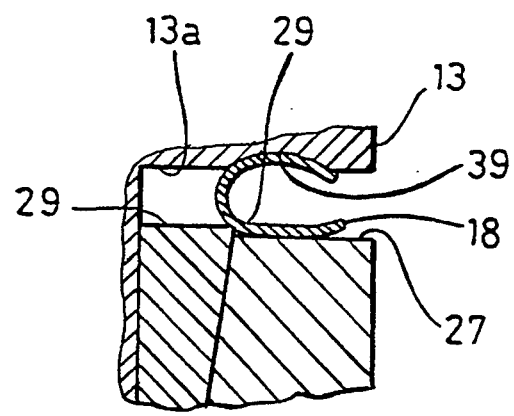
FIG. 5 is a drawing showing a sealing structure between the first insulating spacer and a diffused-diameter portion of the inner electrode.

As shown in FIG. 5, the diffused-diameter portion 13 of the inner electrode is provided with a concave portion 39 having for example a curved section at a portion corresponding to the first sealing ring 18 on the sealing surface 13a thereof, so that the first sealing ring 18 can be held in the concave portion 39 with being engaged while the step 30 of the first insulating spacer 19 and thus a position of the sealing ring 18 can be fixedly set. Accordingly, not only the airtightness in this portion can be improved but also a position of the inner electrode 11 within the pressure container 1 can be fixedly determined, whereby a definite call constant valve can be obtained and thus a highly accurate measurement can be achieved. In addition, in this preferred embodiment, as shown in FIG. 2, a concave portion 40 similar to the concave portion 39 is formed also in a step 6a of the cylindrical member 6 so as to fixedly set a position of the second sealing ring 31.

Figure 6:
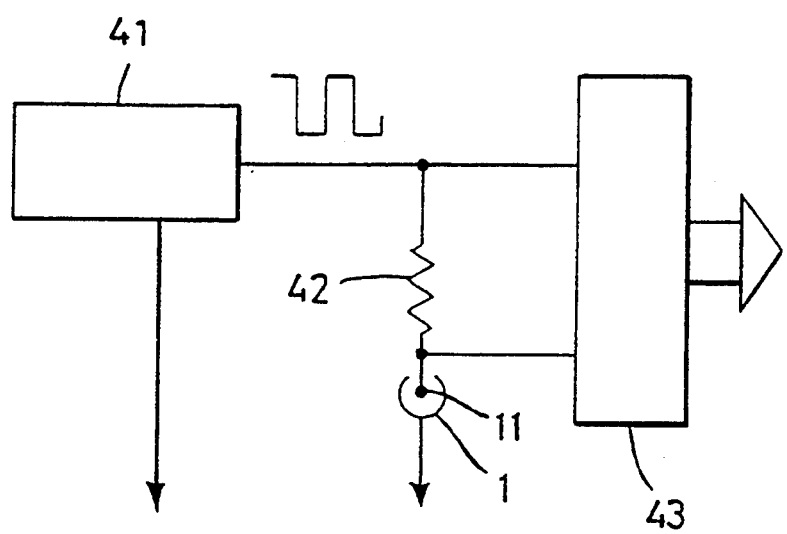
FIG. 6 is a circuit diagram showing one example of an electric construction in the case where an electric conductivity is measured by the use of the cell.

FIG. 6 is a circuit diagram showing one example of an electric construction in the case where an electric conductivity is measured by the use of the cell A. Referring to FIG. 6, reference numeral 41 designates a transmitter transmitting an alternating signal of for example about 900 Hz which is applied to the inner electrode 11. The pressure container 1 serving also as the outer electrode is grounded. In addition, reference numeral 42 designates a fixed resistance. Voltages at both ends of the fixed resistance 42 are put in a processor 43 as detected outputs.

Figure 7:
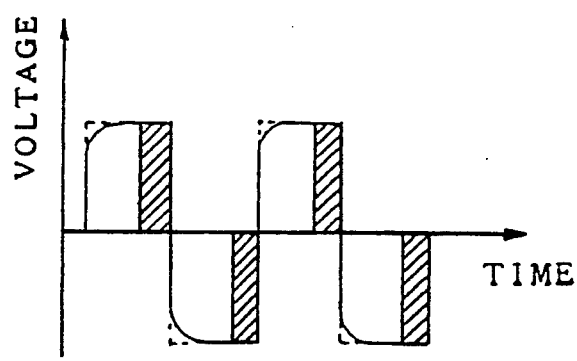
FIG. 7. is a drawing showing one example of a detected output.

FIG. 7 shows one example of the detected outputs. However, in the case where the pressure container 1 is made of stainless steel, if the alternating voltage of about 900 Hz is applied between the inner electrode and the outer electrode in the above described manner, the detected outputs are influenced by a dielectric constant to deteriorate a surmounting, whereby resulting in an error. In order to prevent this, for example it is thought to coat the inner surface of the pressure container 1 with platinum but this is very expensive.

So, according to the present invention, in the processor 43 a synchronism with a transmission frequency is conducted so as to avoid the portions wherein the wave form is disturbed, as signals and to take out merely shaded portions in FIG. 7 as signals, whereby solving a problem that the surmounting is deteriorated. In addition, such a taking-out of signals is effective also in the case where the inner surface of the pressure container 1 is subjected to the electro-polishing and the like taking the corrosion resistance and the chemical resistance into consideration.

Figure 8:
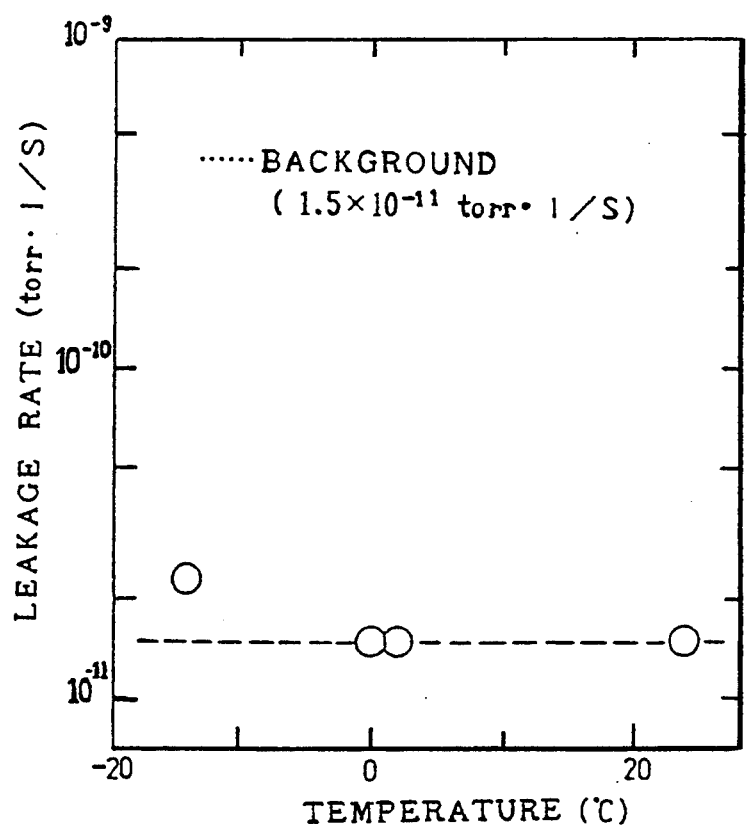
FIG. 8 is data showing a leakage rate of the cell.

FIG. 8 is data showing measured results on an airtightness of a cell A having the above described construction. As shown in FIG. 8, the cell A exhibits a slight increase of leakage rate at $-10°$ C. or less but this does not have substantial influence upon the measurement, that is it is found that the cell A is remarkably superior in airtightness. In addition, a plot at the leakage rate of $1.5 \times 10^{-11}$ Torr· l/s shows a detection limit of a He leak detector.

In addition, in the case where the airtightness within the pressure container 1 is insufficient, not only the liquid introduced into the pressure container 1 is leaked out but also water outside of the pressure container 1 can be diffused into the pressure container 1 by a differential concentration. As a result, not only an error of measurement is produced but also the piping system incorporated in the pressure container 1 can be damaged.

Figure 9:
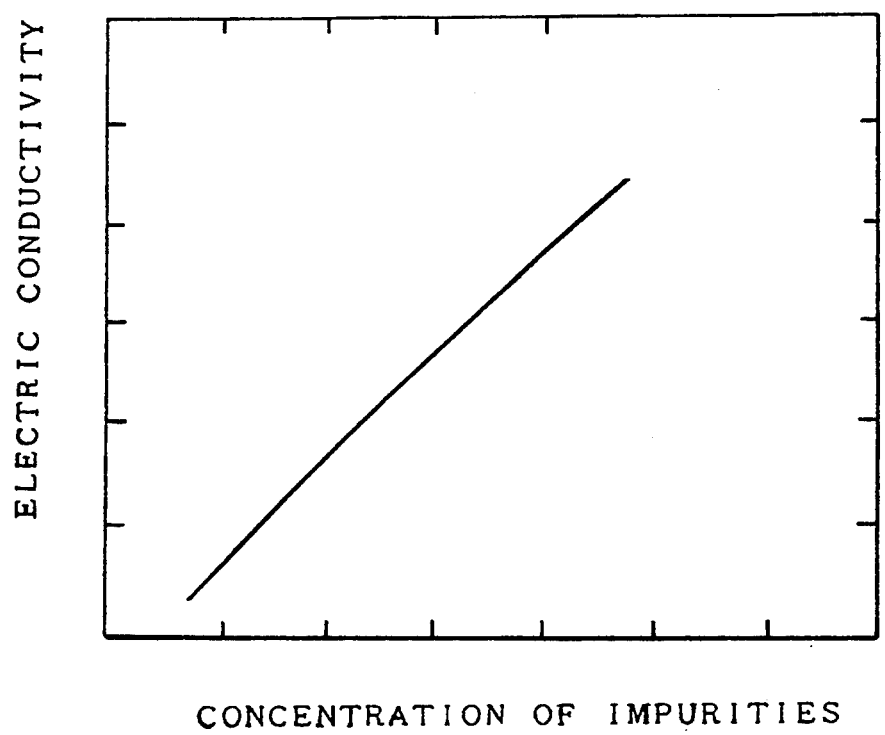
FIG. 9 is a diagram showing a relationship between a concentration of impurities and an electric conductivity in case of liquefied hydrogen chloride.

In a process, in which the liquid to be measured is introduced into and guided out from the pressure container 1, its electric conductivity is measured by means of the pressure container 1 and the inner electrode 11 but the measured electric conductivity can be easily converted into a concentration of impurity by data showing for example a relation between a concentration of impurity in liquefied halogen gases and an electric conductivity with a logarithm of concentration of water as an axis of abscissa and a logarithm of electric conductivity as an axis of ordinate, as shown in FIG. 9, and thus a concentration of a very small quantity of impurities contained in the liquid to be meaasured can be measured.

Because, in the case where water exists in the liquefied gases, such as liquefied hydrogen chloride, the electric conductivity is greatly change due to the dissociation as shown by the following chemical equation (1). In addition, it goes without saying that the electric conductivity is greatly changed due to the dissociation of merely water.

$$HCl + H_2O \rightleftharpoons H_3O^+ + Cl^-$$ [chemical equation (1)]

In addition, in the case where the impurities, such as $H_2SO_4$ and $SiO_2$, exist in liquefied hydrogen chloride, water is produced to be dissociated in the same manner as above described, as shown by the following chemical equations (2), (3), whereby greatly changing the electric conductivity, and thus the concentration of impurities, such as $H_2SO_4$ and $SiO_2$, can be measured in the form of a value converted into water.

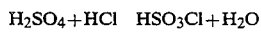
$$H_2SO_4 + HCl \rightleftharpoons HSO_3Cl + H_2O$$ [chemical equation (2)]

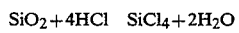
$$SiO_2 + 4HCl \rightleftharpoons SiCl_4 + 2H_2O$$ [chemical equation (3)]

Figure 10:
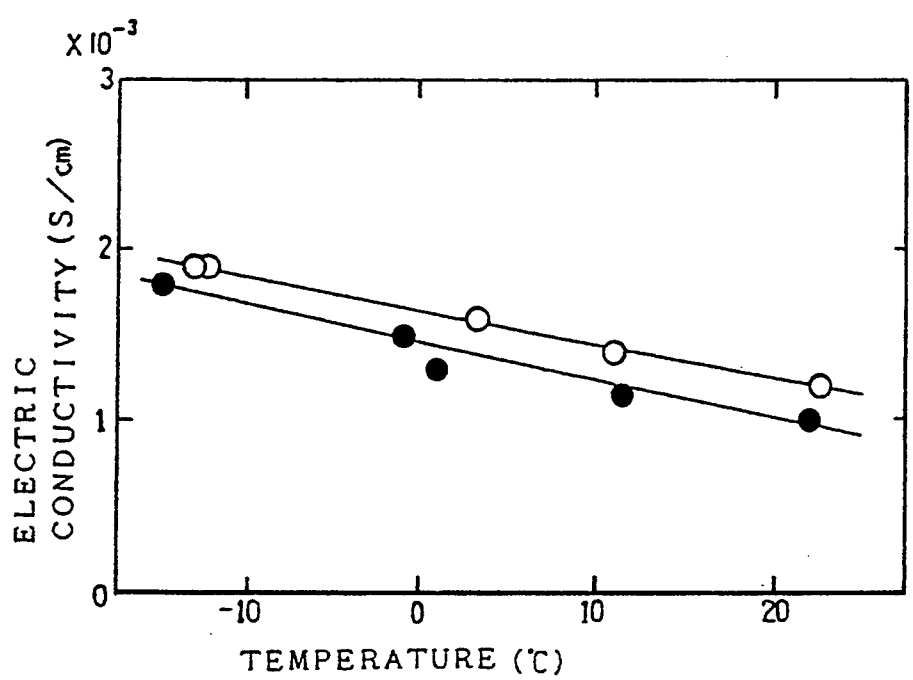
FIG. 10 is a diagram showing a relationship among a quantity of impurities and a temperature and the electric conductivity.

Furthermore, FIG. 10 plots a relation between a temperature and an electric conductivity for two kinds of liquefied hydrogen chloride gas. In order to liquefy chemical substances, which are gaseous at normal temperature and pressure, they are pressurized or cooled but the electric conductivity is changed with a temperature-change, as shown in FIG. 10, so that it is desirable to keep the temperature constant or compensate the electric conductivity by the use of the data showing a relation between a temperature and an electric conductivity for the liquefied hydrogen chloride gas as shown in for example FIG. 10.

In addition, not only the pressure container 1 is made of corrosion-resisting metal but also the inner surface of the pressure container 1 and the outer surface of the inner electrode 11 are subjected to the electro-polishing, the oxidative passivating treatment or the fluorinative passivating treatment, so that, even though the impurities are contained in the liquefied gases, the impurities are not adsorbed on and desorbed from the pressure container 1 and the inner electrode 11 as measuring electrodes and the cell A itself does not generate impurities and additionally also corrosive gases can be adopted as an object to be measured.

In addition, in the above described preferred embodiment, in the cylindrical member 6 connected with the pressure container 1 the first sealing ring 18 and the first stepped insulating spacer 19 are put on one side of the inner electrode 11 so that the first sealing ring 18 may be closer to the diffused-diameter portion 13 of the inner electrode, the second sealing ring 31 being put on the reduced-diameter portion 19A of the first insulating spacer 19, the second stepped insulating spacer 32 and the thrust bearing 37 being put on the other side of the inner electrode 11 so that the second insulating spacer 32 may be closer to the diffused-diameter portion 13 of the inner electrode, and the cap nut 35 screwed on the cylindrical member 6 being screwed up to put the first sealing ring 18 between the first insulating spacer 19 and the diffused-diameter portion 13 of the inner electrode and the second sealing ring 31 between the stepped portion 6a of the cylindrical member 6 and the first insulating spacer 32, so that the high airtightness can be kept within the pressure contaienr. For example, the leak rate is reduced to the detection limit (about $1.5 \times 10^{-11}$ Torr·l/s or less) of the He leak detector and thus not only the liquefied gas can be prevented from being leaked out of the pressure container 1 but also gases can be prevented from entering the pressure container 1 from outside.

And, the stepped first insulating spacer 19 comprises the cylindrical reduced-diameter member 20 airtightly put in the separate cylindrical diffused-diameter member 21 having a larger diameter and a smaller length as compared with those of the cylindrical reduced-diameter member 20 in a tapered manner and comprises the reduced-diameter portion 19A and the diffused-diameter portion 19B, so that the diffused-diameter portion 19A and the reduced-diameter portion 19B can be individually finished, in particular both end faces 27 and 28 of the diffused-diameter portion 19B as the sealing surfaces of the first insulating spacer 19 can be mirror-finished. Accordingly, it is unnecessary to press the sealing rings 18 and 31 by an excessive force and thus the first insulating spacer 19 is not damaged.

In addition, since the diffused-diameter portion 13 of the inner electrode is provided with the concave portion 39 on the sealing surface 13a therof to fixedly hold the first sealing ring 18, not only an airtightness can be improved but also a positional relation between the inner electrode 11 and the pressure container 1 as the outer electrode can be fixedly set at the desired positional relation, so that the measurement can be achieved in higher accuracy. Furthermore, the thrust bearing 37 is provided between the cap nut 35 and the second insulating spaver 32, so that an advantage occurs also in that a turning force of the cap nut 35 does not directly act upon the second insulating spacer 32.

The cell A can be used for not only measuring a very small quantity of impurities contained in the chemcial substances, which are gaseous at normal temperature and pressure, but also measuring the electric conductivity in the control of water quality of industrial water, water supplied for a boiler, various kinds of washing water and the like, in particular suitably used for measuring the electric conductivity of liquids, which exist under the high-temperature and high-pressure condition, such as a primary cooling water in a nuclear power plant.

Althogh the stepped first insulating spacer 19 to be put on the inward portion 16 of the inner electrode comprises the cylindrical reduced-diameter member 20 airtightly put in the separate cylindrical diffused-diameter member 21 having a larger diameter and a smaller length as compared with those of the cylindrical reduced-diameter member 20 in a tapered manner so as to form the reduced-diameter portion 19A and the diffused-diameter portion 19B in the above described preferred embodiment, a first insulating spacer 51 having the following construction may be used.

Figure 11:
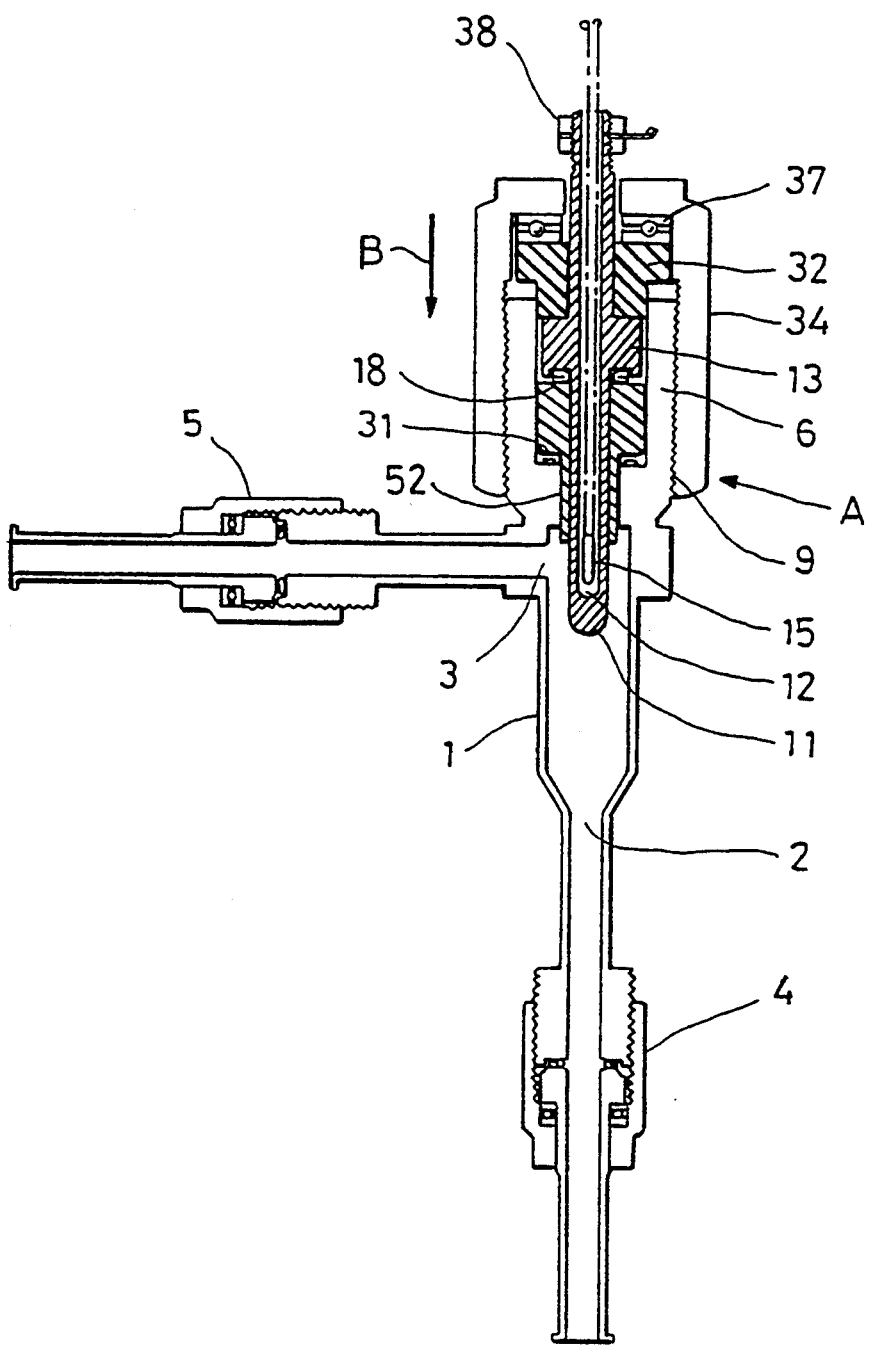
FIG. 11 is a longitudinal sectional view showing an electric conductivity-measuring cell.
Figure 12:
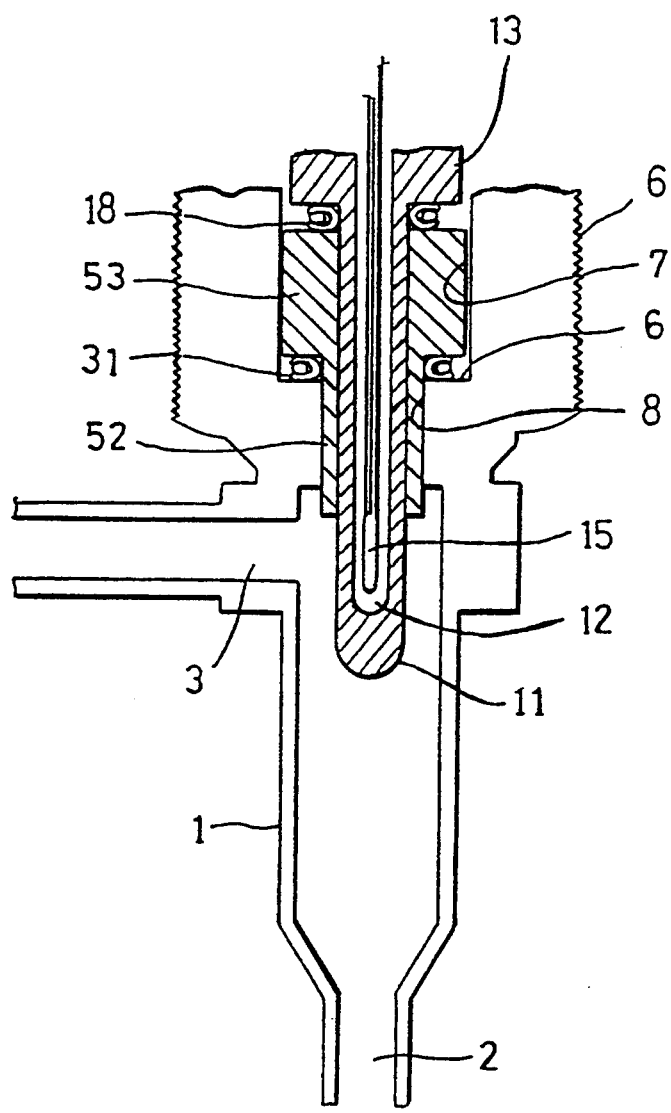
FIG. 12 is a longitudinal sectional view showing a construction of essential parts of the cell.
Figure 13:
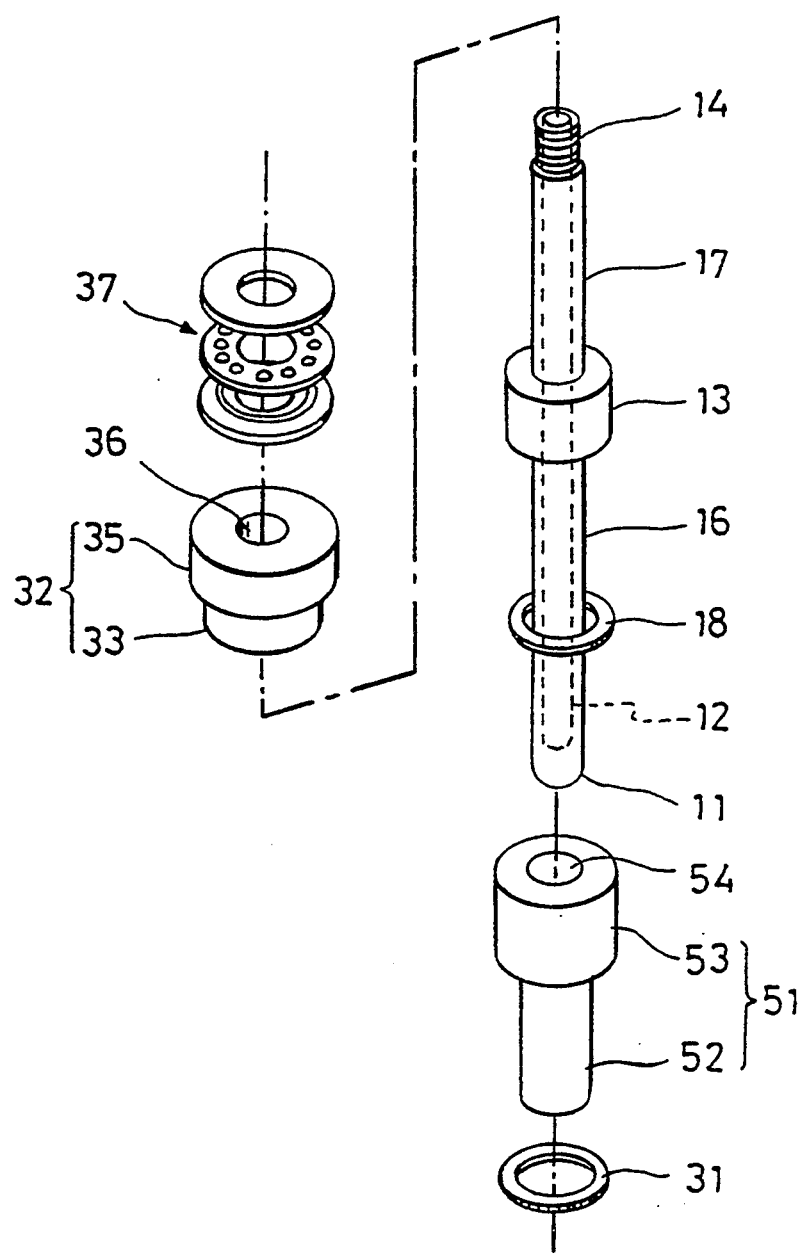
FIG. 13 is a disintegrated perspective view showing a construction of an inner electrode and a sealing construction.

That is to day, FIGS. 11 to 13 show a second preferred embodiment of the present invention. The first insulating spacer 51 in this preferred embodiment comprises a reduced-diameter portion 52 having a diameter slightly smaller than that of a hole 8 provided between a pressure container 1 and a cylindrical member 6 and a diffused-diameter portion 53 having a diameter larger than that of the reduced-diameter portion 52 but slightly smaller than that of a hole 7 of the cylindrical member 6. The spacer 51 is provided with a hole 54 having a diameter slightly larger that of an inward portion 16 of an inner electrode passing therethrough. The first insulating spacer 51 is made of highly insulating materials, such as ceramics, and an outer surface thereof including both end faces is mirror-finished.

The reduced-diameter portion 52 of the first insulating spacer 51 is, as shown in FIGS. 11 and 12, inserted into the hole 8 of the cylindrical member 6 so that a pointed end thereof may arrive at the vicinity of an outlet port 3 of the pressure container 1. Although a cell constant is determined by areas of the inner and outer electrodes and a distance from the inner electrode to the outer electrode, as above described, it can be regulated also by regulating a length of the reduced-diameter diameter portion 52 of the first insulating spacer 51 in addition to regulating a length of the inner electrode 11. In addition, the reduced-diameter portion 52 reduces a contribution to the cell constant in the portion serving as a stagnant or dead space portion of the liquefied gas in the cell by increasing a substantial length between the inner electrode and the outer electrode in the portion positioned above the outlet port 3 within the pressure container 1 to improve an accuracy of measurement of an electric conductivity meter.

Besides, in this preferred embodiment, other constructions are the same as in the first preferred embodiment, so that they are designated by the same reference numerals as in the first preferred embodiment and their detail descriptions are omitted. The operation and effects by this preferred embodiment are almost the same as those in the first preferred embodiment, so that their detail description is omitted.

As above described, according to the present invention, the electric conductivity of various kinds of liquid to be measured can be accurately and simply measured. The sizes of the respective portions, in particular the cell constant, are stabilized, so that the electric conductivity of the liquid to be measured can be accurately measured.

In the case where the stepped first insulating spacer to be put on the inward portion of the inner electrode comprises the cylindrical reduced-diameter member airtightly put in the separate cylindrical diffused-diameter member having a larger diameter and a smaller length as compared with those of the cylindrical reduced-diameter member in a tapered manner, the reduced-diameter portion and the diffused-diameter portion can be separately finished, so that they can be more precisely and easily mirror-finished and thus not only the cell can be easily assembled but also the the cell is remarkably improved in yield.

What is claimed is:

1. In an electrical conductivity measuring cell for measuring the conductivity of a fluid, the improvement comprising:
   an inner electrode member;
   a hollow conductive pressure container, all of which serves as an outer electrode, having inlet and outlet ports for fluidic connections and an opening for supporting the inner electrode member for fluidic contact;

a first support member extending into the opening and the hollow pressure container and surrounding the inner electrode member sufficiently to provide a predetermined cell constant;

a second support member extending about the first support member in the opening;

sealing means for sealing the first support member, and means for exerting a force to hold the respective inner electrode member and first and second support members sealingly connected to the hollow pressure container to provide a leakage rate of helium in the approximate range of $1.5 \times 10^{-10}$ Torr·l/s.

2. The invention of cliam 1 wherein the inner electrode member is hollow and a temperature sensor is contained within that portion of the inner electrode member that is available for fluidic contact.

3. The invention of claim 1 wherein the first support member has a conical portion.

4. The invention of claim 1 wherein the second support member has a central conical tapered opening.

5. The invention of claim 1 wherein the sealing means includes a first and second annular sealing ring mounted at either end of the second support member.

6. The invention of claim 1 wherein the inner electrode member has an enlarged step portion for engaging the sealing means with the second support member.

7. The invention of claim 1 wherein the inner surface of the hollow pressure container, which is in contact with the fluid when fluid is being measured in the cell, and an outer surface of the electrode member which is in contact with the fluid when fluid is being measured in the cell, are subject to one of the following surface treatments to provide a characteristic surface structure resulting from a surface treatment of electro-polishing, an oxidative passivity treatment and fluorinative passivity treatment.

8. The invention of claim 1 wherein the means for exerting a force includes an insulating spacer member, a thrust bearing member and a cap member fastening across the pressure container opening.

9. The invention of claim 1 wherein a central conical opening is provided in the second support member of a lesser diameter that a surface diameter of the first support member conical portion.

10. In an electrical conductivity measuring cell for measuring the conductivity of a fluid, the improvement comprising:

an elongated inner electrode member having an enlarged annular portion along its length;

a hollow conductive pressure container, all of which acts as an outer electrode, having inlet and outlet ports for fluidic connections to a fluid to be measured and an opening for supporting the electrode member to be cantilevered into the hollow portion of the pressure container in an insulating arrangement from the pressure container;

a support assembly of an insulating material mounted in the pressure container opening and along a portion of the cantilevered inner electrode member and including an upper enlarged annular portion and a lower reduced annular portion with an internal opening of a size complementary to an outer surface dimension of the elongated electrode member;

sealing means for sealing the support assembly to the electrode member to provide a leakage rate in the range of $1.5 \times 10^{-11}$ Torr·l/s of helium; and means for securing the support assembly and electrode member in the opening while insulating the electrode member from the pressure container.

11. The invention of claim 10 wherein an inner surface of the hollow pressure container, which is in contact with the fluid when fluid is being measured in the cell, and an outer surface of the electrode member which is in contact with the fluid when fluid is being measured in the cell, are subject to one of the following surface treatments to provide a characteristic surface structure resulting from a surface treatment of electro-polishing, an oxidative passivity treatment and a fluorinative passivity treatment.

12. The invention of claim 10 wherein the means for securing includes an insulating spacer member, a thrust bearing member and a cap member that can be fastened across the pressure container opening.

13. The invention of claim 10 wherein the support assembly includes a unitary member.

14. The invention of claim 10 wherein the support assembly includes a first support member with a reduced annular portion, including a conical configuration, and a second support member with a cylindrical outer surface and a tapered central conical opening for engaging the conical configuration of the first support member.

15. The invention of claim 14 wherein the sealing means includes first and second annular sealing rings mounted at either end of the second support member.

16. The invention of cliam 14, wherein the electrode member annular portion includes an enlarged step portion for engaging the sealing means with the second support member.

17. The invention of cliam 15 wherein the electrode member is hollow and a temperature sensor is contained within that portion of the electrode member that is available for fluidic contact.

18. An electrical conductivity measuring cell for measuring the conductivity of a fluid, the improvement comprising:

a hollow inner electrode member having an enlarged annular portion along its length;

a hollow conductive pressure container, all of which serves as an outer electrode, having an inlet port for receiving a pressurized liquid to be measured and an outlet port for discharging the pressurized liquid after it has been measured and an opening for supporting the hollow inner electrode member for fluidic contact in an insulating arrangement from the pressure container;

a temperature measuring means inserted into the hollow electrode member so that the temperature is measured within that portion of the electrode member that is available for fluidic contact;

a support assembly of an insulating material that is mounted in the pressure container opening and includes an upper enlarged annular portion and a lower reduced annular portion with an internal opening of a size complementary to an outer surface dimension of the elongated electrode member;

first sealing means for sealing the support assembly to the electrode member in a substantially gas tight manner;

second sealing means for sealing the support assembly to the hollow pressure container in a substantially gas tight manner, the first and second sealing means providing a leakage rate in the range of $1.5 \times 10^{-11}$ Torr·l/s of helium; and means for exerting a force to hold the support assembly and electrode member in the opening while insulating the electrode member from the pressure container.

19. The invention of claim 18 wherein an inner surface of the hollow pressure container, which is in contact with the liquid when liquid is being measured in the cell, and an outer surface of the electrode member which is in contact with the liquid when fluid is being measured in the cell, are subject to one of the following surface treatments to provide a characteristic surface structure resulting from a surface treatment of electropolishing, an oxidative passivity treatment and a fluorinative passivity treatment.

20. In an electrical conductivity measuring cell for measuring the conductivity of a fluid, the improvement comprising:

an inner electrode member;

a hollow conductive pressure container, all of which serves as an outer electrode, having inlet and outlet ports for fluidic connections and an opening for supporting the inner electrode member for fluidic contact;

a first support member, having a conical portion, extending into the opening and surrounding the inner electrode member;

a second support member extending about the first support member in the opening;

sealing means for sealing the first support member; and means for exerting a force to hold the respective inner electrode member and first and second support members sealingly connected to the hollow pressure container.

21. The invention of claim 20 wherein a central conical opening is provided in the second support member of a lesser diameter than a surface diameter of the first support member conical portion.

22. The invention of claim 20 wherein an inner surface of the hollow pressure container, which is in contact with the fluid when fluid is being measured in the cell, and an outer surface of the electrode member which is in contact with the fluid when fluid is being measured in the cell, are subject to one of the following surface treatments to provide a characteristic surface structure resulting from a surface treatment of electropolishing, an oxidative passivity treatment and a fluorinative passivity treatment.

23. The invention of claim 20 wherein the sealing means includes first and second annular sealing rings mounted at either end of the second support member.

24. In an electrical conductivity measuring cell for measuring the conductivity of a fluid, the improvement comprising:

an inner electrode member;

a hollow conductive pressure container, all of which serves as an outer electrode, having inlet and outlet ports for fluidic connections and an opening for supporting the inner electrode member for fluidic contact;

a first support member extending into the opening and surrounding the inner electrode member;

a second support member extending about the first support member in the opening;

sealing means for sealing the first support member, wherein the inner electrode member has an enlarged step portion for engaging the sealing means with the second support member; and means for exerting a force to hold the respective inner electrode member and first and second support members sealingly connected to the hollow pressure container.

25. The invention of claim 24 wherein an inner surface of the hollow pressure container, which is in contact with the fluid when fluid is being measured in the cell, and an outer surface of the electrode member which is in contact with the fluid when fluid is being measured in the cell, are subject to one of the following surface treatments to provide a characteristic surface structure resulting from a surface treatment of electropolishing, an oxidative passivity treatment and a fluorinative passivity treatment.

26. The invention of claim 24 wherein the sealing means includes first and second annular sealing rings mounted at either end of the second support member.

* * * * *